United States Patent
Boyd-Moss et al.

(10) Patent No.: US 6,631,801 B2
(45) Date of Patent: Oct. 14, 2003

(54) TRANSPORT PACKAGE

(75) Inventors: Graeme Boyd-Moss, Waterlooville (GB); Roderick I. Davidson, Petersfield (GB)

(73) Assignee: Inspiral, LLC, Hartsville, SC (US)

( * ) Notice: Subject to any disclaimer, the term of this patent is extended or adjusted under 35 U.S.C. 154(b) by 0 days.

(21) Appl. No.: 09/758,921

(22) Filed: Jan. 11, 2001

(65) Prior Publication Data

US 2001/0019024 A1 Sep. 6, 2001

(30) Foreign Application Priority Data

| Feb. 9, 2000 | (GB) | 0002884 |
|---|---|---|
| Apr. 20, 2000 | (GB) | 0009777 |
| Oct. 3, 2000 | (GB) | 0024166 |
| Oct. 3, 2000 | (GB) | 0024168 |

(51) Int. Cl.[7] .............................................. B65D 81/26
(52) U.S. Cl. ...................................... 206/204; 206/438
(58) Field of Search ................................ 206/204, 223, 206/438, 363, 364, 365, 366, 370, 497; 220/23.91, 23.83, 212

(56) References Cited

U.S. PATENT DOCUMENTS

| 1,408,757 A | | 3/1922 | Metzger |
| 1,750,074 A | | 3/1930 | Warner |
| 1,923,426 A | | 8/1933 | Eggerss |
| 2,283,867 A | | 5/1942 | Flosdorf et al. |
| 3,014,630 A | | 12/1961 | Whelan et al. |
| 3,559,872 A | | 2/1971 | Riboud |
| 3,990,872 A | | 11/1976 | Cullen |
| 4,150,744 A | | 4/1979 | Fennimore |
| 4,156,022 A | * | 5/1979 | Nugent .................. 206/583 |
| 4,256,770 A | | 3/1981 | Rainey |
| 4,356,935 A | * | 11/1982 | Kamin .................. 206/384 |
| 4,679,688 A | | 7/1987 | Soderholm et al. |
| 4,748,069 A | | 5/1988 | Cullen |
| 4,817,815 A | * | 4/1989 | Stahlecker ............. 220/203.01 |
| 4,853,266 A | | 8/1989 | Cullen |
| 4,927,010 A | | 5/1990 | Kannankeril |
| 4,940,135 A | * | 7/1990 | Hall ........................ 206/3 |

(List continued on next page.)

FOREIGN PATENT DOCUMENTS

| CA | 1 253 089 A | | 4/1989 |
| DE | 36 24 410 A1 | * | 1/1988 |
| EP | 0368007 | | 5/1990 |
| EP | 0485289 | | 5/1992 |
| EP | 0189406 | | 3/1998 |
| FR | 682 144 A | * | 5/1930 |
| FR | 2 248 989 A | * | 5/1975 |
| FR | 2681839 | | 4/1993 |
| GB | 2066209 | | 7/1981 |
| GB | 2154982 | | 9/1985 |
| WO | 8501272 | | 3/1995 |
| WO | 9516620 | | 6/1995 |
| WO | 9838040 | | 9/1998 |

*Primary Examiner*—Shian Luong
(74) *Attorney, Agent, or Firm*—Alston & Bird LLP (57) ABSTRACT

A transport package for containing sample tubes and similar materials prone to leakage comprises a rigid, crush resistant tube e.g. wound from cardboard and having an integrally formed super-absorbent lining, the ends of the tube being closed by end caps. The transport package may be placed into a protective envelope comprising a closely fitting pouch for the package and a further pouch for accompanying documentation. Several such packages or packages in envelopes may be placed in a tertiary container comprising a tube forming a main body of the tertiary container. This tube may be divided into two sections, held together by a shrink fit band or outer covering. One end of the tube is formed with a permanent closure and the other end is closable by a lid having an inner rim with a lip that engages between the two sections of the tube.

27 Claims, 6 Drawing Sheets

U.S. PATENT DOCUMENTS

| | | |
|---|---|---|
| 4,941,574 A | 7/1990 | Meehan |
| 4,969,750 A | 11/1990 | Russo et al. |
| 4,998,621 A | 3/1991 | Meehan |
| 5,069,694 A | 12/1991 | Cullen et al. |
| 5,160,022 A | 11/1992 | Mennella |
| 5,199,795 A | 4/1993 | Russo et al. |
| 5,203,492 A * | 4/1993 | Schellenberg ............... 220/678 |
| 5,251,755 A * | 10/1993 | Kausch ....................... 206/455 |
| 5,279,421 A | 1/1994 | Gouge et al. |
| 5,284,621 A | 2/1994 | Kaufman |
| 5,330,047 A | 7/1994 | Gouge et al. |
| 5,403,096 A | 4/1995 | Aagesen |
| 5,427,238 A | 6/1995 | Weiss |
| 5,451,437 A | 9/1995 | Insley et al. |
| 5,503,835 A | 4/1996 | Van Roekel |
| 5,603,401 A * | 2/1997 | Brunner |
| 5,620,759 A | 4/1997 | Insley et al. |
| 5,637,364 A * | 6/1997 | Akao et al. .................. 206/389 |
| 5,641,496 A | 6/1997 | Van Roekel |
| 5,660,868 A | 8/1997 | Yeager |
| 5,687,839 A * | 11/1997 | Gnau et al. .................. 206/204 |
| 5,691,015 A | 11/1997 | Tsukamoto et al. |
| 5,697,200 A | 12/1997 | Insley et al. |
| 5,827,586 A | 10/1998 | Yamashita et al. |
| 5,833,058 A | 11/1998 | Mabry |
| 5,885,673 A * | 3/1999 | Light et al. .................. 206/455 |
| 5,898,358 A * | 4/1999 | Tompkins et al. ........... 337/163 |
| 5,984,087 A | 11/1999 | Hacikyan |
| 6,308,827 B1 * | 10/2001 | Hacikyan .................... 206/204 |
| 6,446,794 B1 | 9/2002 | Hacikyan |

* cited by examiner

TRANSPORT PACKAGE

TECHNICAL FIELD

The present invention relates to a transport package.

BACKGROUND OF THE INVENTION

Transport of hazardous goods, in particular medical samples, is subject to regulation. Security against leakage, in general, and in particular against crush induced leakage is called for. There are different levels of regulation for different samples. The more hazardous is the sample, the more severe is the regulation, for example IATA Transport of Dangerous Goods Regulations 602 and 650.

A known medical sample transport package, to meet the severe regulations, includes:

A closed sample-tube containing the sample;

An envelope of absorbent material, into which the sample-tube is placed;

An inner plastics material bottle, which is sealable with the sample-tube and envelope enclosed;

An outer plastic bottle of heavier construction to provide crush strength;

A cardboard box to receive the outer bottle for its despatch through the mail, which routinely includes air freighting.

Such a package is inevitably expensive.

U.S. Pat. No. 5,984,087 (Hacikyan) describes a packaging container comprising an envelope of water insoluble material having a lining comprising a water soluble material trapping an absorbent material. In the event of leakage the water soluble material dissolves releasing the absorbent material which can soak up leaked liquid to prevent its release from the envelope. Similar products are disclosed in U.S. Pat. No. 4,748,069 and U.S. Pat. No. 4,853,266 (both to Cullen). A drawback to the products disclosed in these three patents is that the water soluble material needs time to dissolve before the water absorbent material is released, so giving liquid time to migrate and find escape routes. A further drawback is that these packages do not provide significant protection against crush induced leakage.

International Patent Application WO95/16620 (Noax AB) discloses a package comprising a liquid impermeable layer and an absorbent layer, the absorbent layer possibly comprising super-absorber fibres or powder. Such a package has the drawback that such a package does not provide significant protection against crush induced leakage.

One object of the invention is to provide an improved transport package having sufficient strength against crush induced leakage.

A further object of the invention is provide an improved transport package providing close contact between super-absorbent material and a sample tube to be transported.

One of the inventors hereto (Davidson) has previously described how super-absorbent materials can be used in the packaging of meat (WO98/38040) and has realised that similar technology can be applied with advantage to the somewhat different art of transporting medical samples.

SUMMARY OF THE INVENTION

In a first aspect, the transport package of the invention for containing goods such as sample tubes and other materials presenting a leakage hazard, comprises:

a crush resistant tube sized to receive the goods;

an absorbent lining formed integrally with the crush resistant tube;

end caps for the crush resistant tube.

Preferably the crush resistant tube is of wound cardboard material, with the absorbent lining being a first winding onto the former for the tube. The cardboard windings of the crush resistant tube can be interspersed with a reinforcement layer, in particular of glass reinforced plastics material. Additionally or alternatively, the cardboard windings can be adhered together with a suitable resin material. As a further alternative, the crush resistant tube may be of plastics material, for example GRP, polyethylene, or epoxy impregnated glass fibre matt. Advantageously use of a transparent plastics material will result in a transparent tube, enabling any leakage to be detected prior to opening of the tube. While the crush resistant tube will typically be circular in cross-section, it may be square or any other shape.

Preferably, the absorbent lining incorporates super-absorbent material, conveniently being an air laid web on a synthetic material non-woven carrier against which the tube is wound, i.e. with non-woven carrier outermost. The super-absorbent material may be in the form of fibre or a powder. Normally the super-absorbent material will be bulked with cellulose material.

When the tube is of cardboard windings, preferably a waterproof layer will be provided between the absorbent layer and the tube to prevent the cardboard being softened by leaking liquid. Advantageously this can be a winding between the absorbent lining first winding, and the cardboard winding for the tube.

Usually the tube will further include an outer waterproof layer. As an alternative a further absorbent layer is wound outside the tube.

Whilst the end caps could be configured to grip the tube either on the outside only or on the inside only, they preferably have an annular, channel-shaped rim for gripping on both the inside and the outside. Further, the end caps can carry on their inside a leakage indicator, for instance a moisture induced colour change ink, the caps being translucent. Such ink then indicates a leak by changing colour as a result of the moisture on the inside of the cap. Alternatively one of the end caps could be a permanently fitted cap, for example a metal cap machined on.

Whilst it is anticipated that the combination of the absorbent inner and outer linings, waterproof layer and the end caps will be adequate, for transport of certain hazardous substances, for example veterinary samples; where additional leak proofing is required, an outer envelope may be provided for the tube. Preferably the outer envelope will be configured to have two pouches, one for the crush resistant tube and the other for accompanying documentation. In the preferred embodiment the two pouches are formed from a single sheet of transparent plastics membrane, the pouches opening onto a central divide. Conveniently, a strip of adhesive is provided along the central divide for sealing both pouches to minimise the possibility of leakage from the tube pouch to the document pouch. Furthermore the pouch is sized to receive the tube as a tight fit. This prevents displacement of the end caps while the tube is in the pouch, further minimising the possibility of leakage. Importantly the envelope prevents the displacement of the end caps during shock, for example a crushing force, by providing a barrier against their movement.

Alternatively or additionally to the outer absorbent layer of the crush resistant tube, the membranes of the tube pouch may be lined with an absorbent web.

Whilst the end caps are configured to grip the tube, to minimise the risk of their accidental removal, by crushing for example, according to a further aspect of the invention, a sheath of rubber or like material may be provided for enclosing the tube. The nature of the rubber, or like material, is such that if it is crushed, it is unlikely to be damaged, but to return to shape after crushing. In this case, if the tube is crushed such that the end caps are displaced by the expulsion of air from the tube, the sheath will urge the end caps to return to their normal position when the crushing force is removed. In addition this sheath also provides a further additional waterproof barrier, further minimising the risk of leakage of the sample. While a closure member may be provided for the sheath, this has found to be unnecessary to its action in retaining the end caps in their position. However a closure member may be provided which will enhance the sheath's use as a further liquid proof barrier. Alternatively the free end of the sheath may be tied after the tube has been placed inside the sheath.

The sheath may be provided additionally or alternatively to the envelope.

In accordance with a particular feature of the invention, the crush resistant tube is provided in combination with tamper evident container therefor.

According to a second aspect of the present invention there is provided a container comprising:

a tube forming the main body of the container, the tube being divided into two sections, a band around the circumference of the tube at an abutment between the two sections of the tube, to hold them in alignment, a lid for closing the tube at one end, the lid including an inner rim for engagement within the tube, the rim having a lip for engagement between the two sections of the tube; and a closure for the other end of the tube.

Whilst it is envisaged that the lip may be discontinuous, preferably it is continuous.

The band may be a sleeve extending along the full length of the tube. Preferably it is a shrink wrap plastics material sleeve. Conveniently it can be used to secure the closure to the other end of the tube.

Usually the rim will be deeper than the one section of the tube closed by the lid for engagement into the other section of the tube.

In use the material to be transported, is placed inside the container, and the end lid is pushed into place. The lip on the lid engages between the two sections of the tube, and is difficult to remove without damaging part of the container.

The rim of the outside surface of the lid has no substantial upstand from the one section of the tube whereby it cannot readily be gripped. Preferably it is tapered at its periphery shallowly to the end of the tube.

When the container reaches its destination, the intended recipient can slit the band at the junction between the two sections of the tube and then remove the lid with the one section of the tube. Any attempt to tamper with the contents of the container is clearly visible from the outside of the container.

Typically the tube will be of wound cardboard material. In some embodiments the tube may be lined with absorbent material, preferably incorporating super-absorbent material. In this embodiment the absorbent lining may be the first winding for the tube. The cardboard winding of the tube may be interspersed with a reinforcement layer, in particular of glass reinforced plastics material. Additionally or alternatively, the cardboard winding can be adhered together with a suitable resin material. As a further alternative the tube may be of plastics material, for example GRP, or epoxy impregnated glass fibre matt.

The closure for the distal end of the main tube will typically be a disc, having the same diameter as the external diameter of the tube. The closure is held in place by the shrink wrap sleeve.

Preferably an upper inner rim of the other section of the tube will be indented to allow ingress of the lip of the lid.

The container may be provided with internal dividers, which can strengthen the tube.

According to a further aspect of the present invention, the crush resistant tube can be configured as a container for the transport and disposal of sharps by providing an aperture in one of the end caps for insertion of the sharp.

The aperture can be in the form of two conjoined circular holes such that a needle, while still attached to a syringe, can be inserted into a larger of the two, pushed into the smaller of the two and thereby disconnected from the syringe and thereafter fall into the container.

Preferably the crush resistant tube is of wound cardboard material, with the absorbent lining being a first winding onto the former for the tube. After use the whole container including the sharps can be incinerated.

Used hypodermic needles will often contain a small amount of blood or drug which has been injected into the patient, and will often have a certain amount of blood on the outside. Similarly used scalpels will often have a small amount of blood or tissue debris adhering to their surface. Advantageously the super-absorbent material in the container will absorb the material, lessening any risk on contamination. In addition, some super-absorbent material has an anti-bacterial effect in their absorption. This will even further lessen the risk of contamination.

Typically the ends cap will be configured such that it is difficult to remove from the tube to prevent access to the sharps. The end cap is provided with an annular lip on its top surface which when closed is flush with the end of the tube. The cap is also provided with an annular lip on its rim for gripping to the inside of the tube. The absorbent material inside the tube is deformed by this lip making removal of the cap more difficult. Furthermore, as the blood etc contamination on the sharps is absorbed by the absorbent material it causes swelling which also enhances the tight fit of the caps. Additionally or alternatively a groove can be provided in the tube into which the annular lip fits, again further increasing the difficulty of removal of the cap.

To reduce the size of the container, in particular for transportation thereof, the tube may be conical.

BRIEF DESCRIPTION OF THE DRAWINGS

To help understanding of the invention, a specific embodiment thereof will now be described by way of example and with reference to the accompanying drawings, in which.

DETAILED DESCRIPTION OF THE INVENTION

Figure 1:
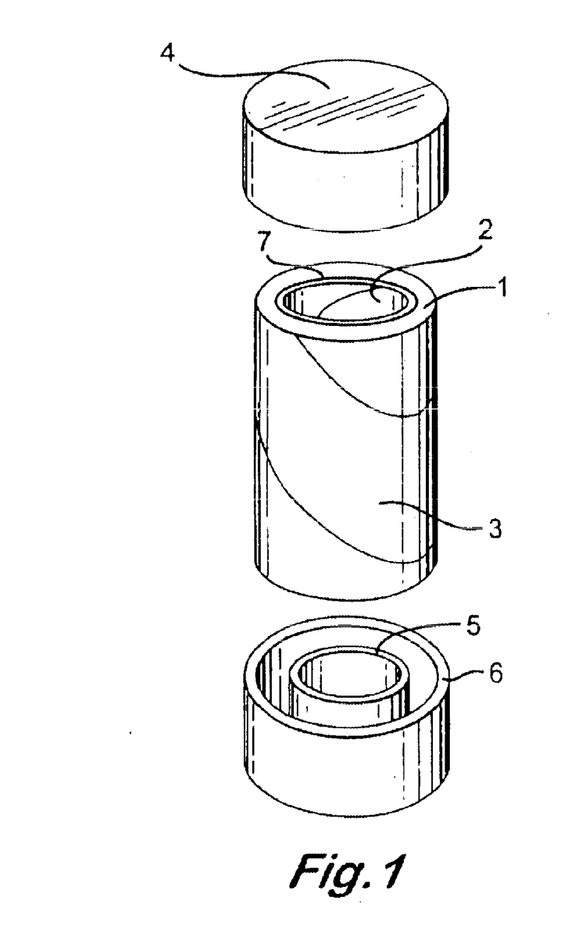
FIG. 1 is an exploded perspective view of a crush resistant tube of the invention.

Referring first to FIG. 1, the crush resistant tube 1 there shown is of wrapped card, typically having an internal diameter of 30 mm and an external diameter of 40 mm, wound on a suitable former and cut to 110 mm lengths. The outer card layers are wound over a first winding which forms an absorbent lining 2. The material forming the wound lining 2 is formed from a web of non-woven carrier—typically polyethylene—having air laid onto it a mixture of cellulose, super-absorbent fibre and a bicomponent fibre as a binder.

A suitable material for the absorbent lining 2 would be the type of absorbent non-woven material disclosed in WO98/3 8040 which comprised a web of:

| | |
|---|---|
| wood pulp fibre | 52% |
| super-absorbent fibre | 30% |
| thermoplastic bonding material | 18% | air laid onto a non-woven base tissue (for example a polyethylene tissue). The super-absorbent fibre is sold under the OASIS trade mark by Technical Absorbents Limited. The thermoplastic bonding material is a hydrophilic bicomponent fibre comprising polyethylene coated polypropylene sold by Danaklon A/S of Varde in Denmark.

However, such a material has only limited absorbency and so a higher proportion of super-absorbent fibre can be used. The absorbency and quantity of the lining material used to wind the tube should preferably be sufficient to absorb the entire contents of any liquid sample container inserted into the tube 1. A preferred composition comprises:

| | |
|---|---|
| Bi-component fibre | approximately 20% |
| Super absorbent fibre | approximately 55% |
| Cellulose | approximately 25% |

This is laid onto the non-woven tissue (for example Licontrol™ available from Jacob Holm industries, Soultz, France). The super-absorbent fibre serves to absorb liquids. The cellulose provides water passage to prevent the super-absorbent fibre blocking the material as it swells on absorbing water. The bi-component fibre bonds the component parts together and provides strength, and the non-woven tissue provides a support for the materials.

A typical formulation would comprise:

| | |
|---|---|
| Bi-component fibre | 25 gsm (grams per square meter) |
| Super absorbent fibre | 62 gsm |
| Cellulose | 30 gsm |
| non-woven tissue | 17 gsm. |

Such super-absorbent containing air laid materials are readily obtainable from manufacturers of air laid products, for example Dan-Webforming Research & Development A/S.

An outer waterproof layer 3 is provided. An inner waterproof layer 7 is also provided between the absorbent lining 2 and the crush resistant tube. Polyethylene end caps 4 are provided. For security in their fitting, they are provided with both inner and outer rims 5,6 for engaging inside and outside the tube 1, the engagement being enhanced in the event of leakage by swelling of the absorbent. Usually, the end caps will be of translucent material, particularly where they are treated inside with colour change ink to indicate leakage. Suitable water sensitive inks are available from For.Tex srl, Fino Momasco, Italy. The crush resistant tube is sized to receive a sample-tube.

Figure 2:
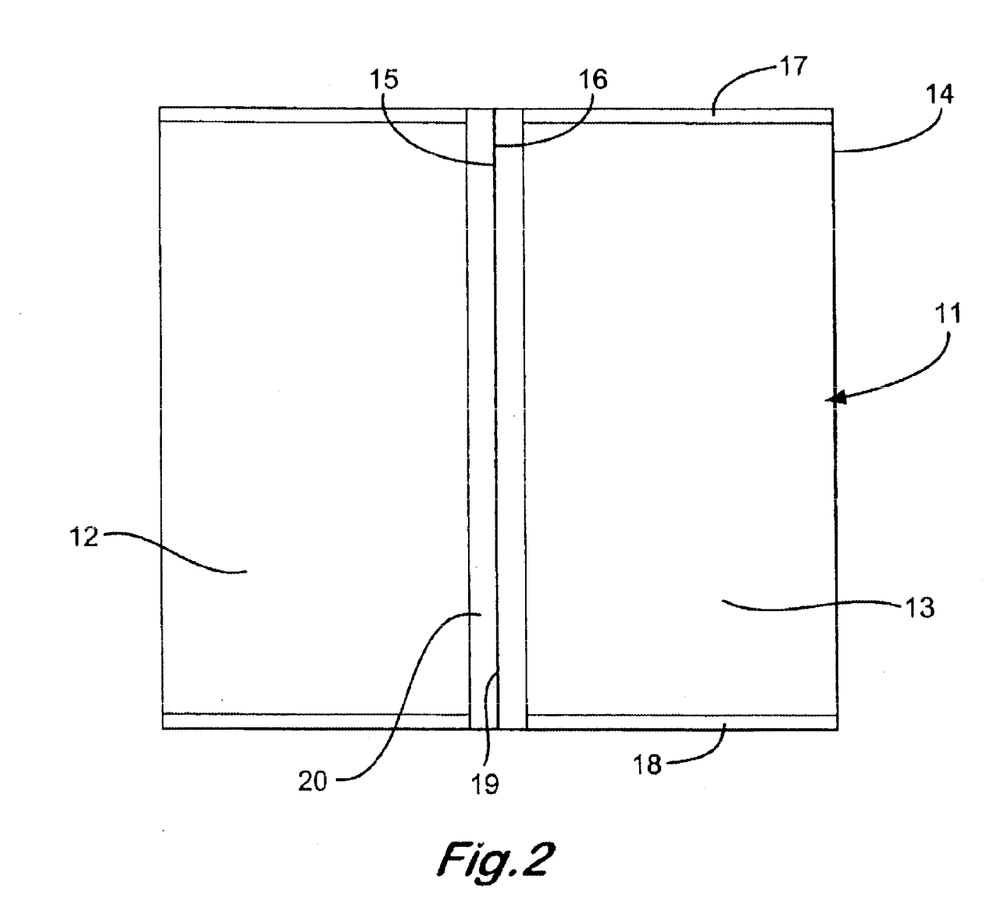
FIG. 2 is a front view of an envelope of the invention.

Turning to FIG. 2, an envelope 11 is shown ready to receive the closed tube. This has two adjacent pouches 12,13. The envelope is formed from a single rectangular sheet of plastics material 14. The two short ends 15, 16 of the plastics sheet are folded to the middle and the upper and lower edges 17, 18 thereof are sealed, providing an envelope with a central divide 19 and two adjacent pouches 12, 13.

Figure 3:
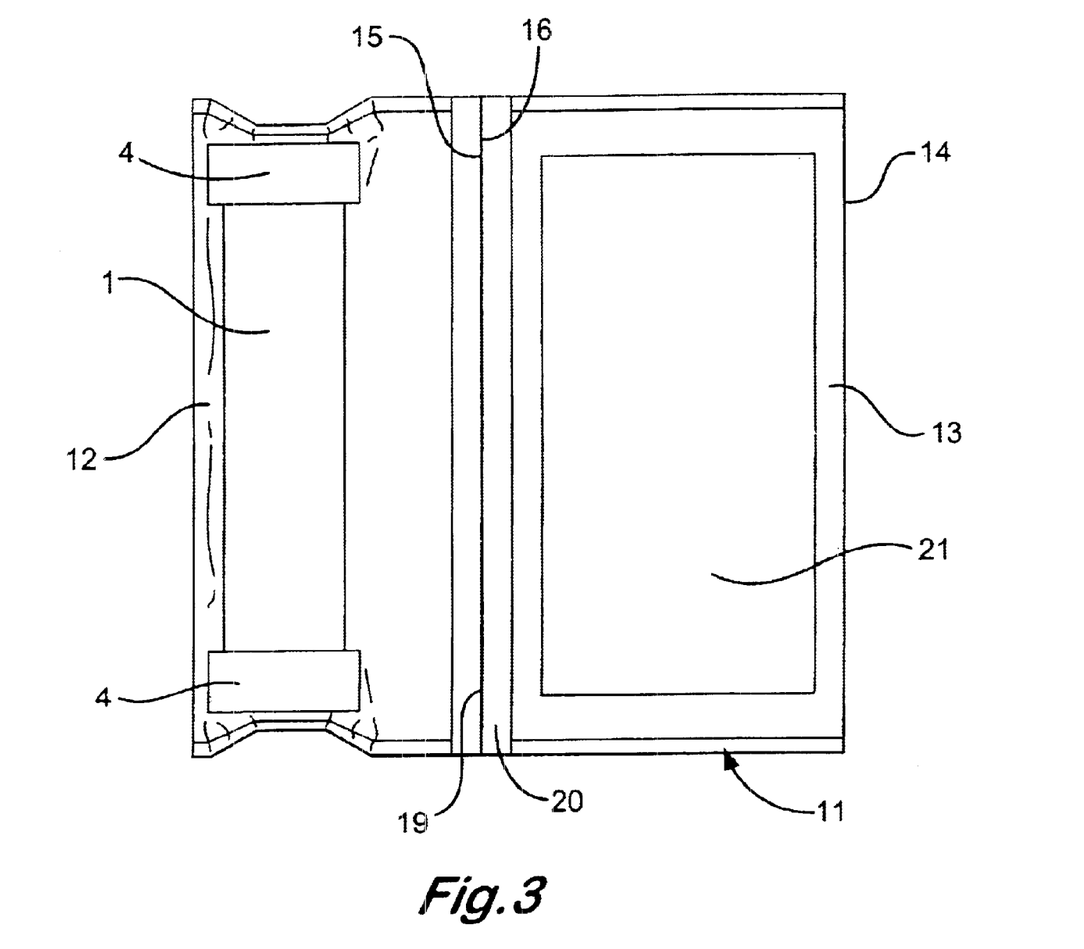
FIG. 3 is a front view of the tube of FIG. 1 in the envelope of FIG. 2.

Referring now to FIG. 3, the tube 1 thereshown is fitted with end caps 4 and sealed into its pouch 12 in the envelope 11. The pouch 12 is sized to receive the tube 1 as a tight fit. This prevents the end caps 4 from being removed while the tube is in the pouch 12, further reducing the possibility of leakage. An adhesive strip 20 is provided along the central divide 19 behind a release paper for sealing the open edges of the pouches 15, 16. The second pouch 13 is used for carrying supporting documentation 21.

In use, the sample tube is contained inside the crush resistant tube 1. Should the contents of the sample tube leak, as a result of poor sealing of it, leaking liquid will be absorbed by the inner lining. Any liquid leaking past the end caps 4 will be trapped in the envelope 11. Thus there is little likelihood of the liquid escaping.

Figures 4, 5:
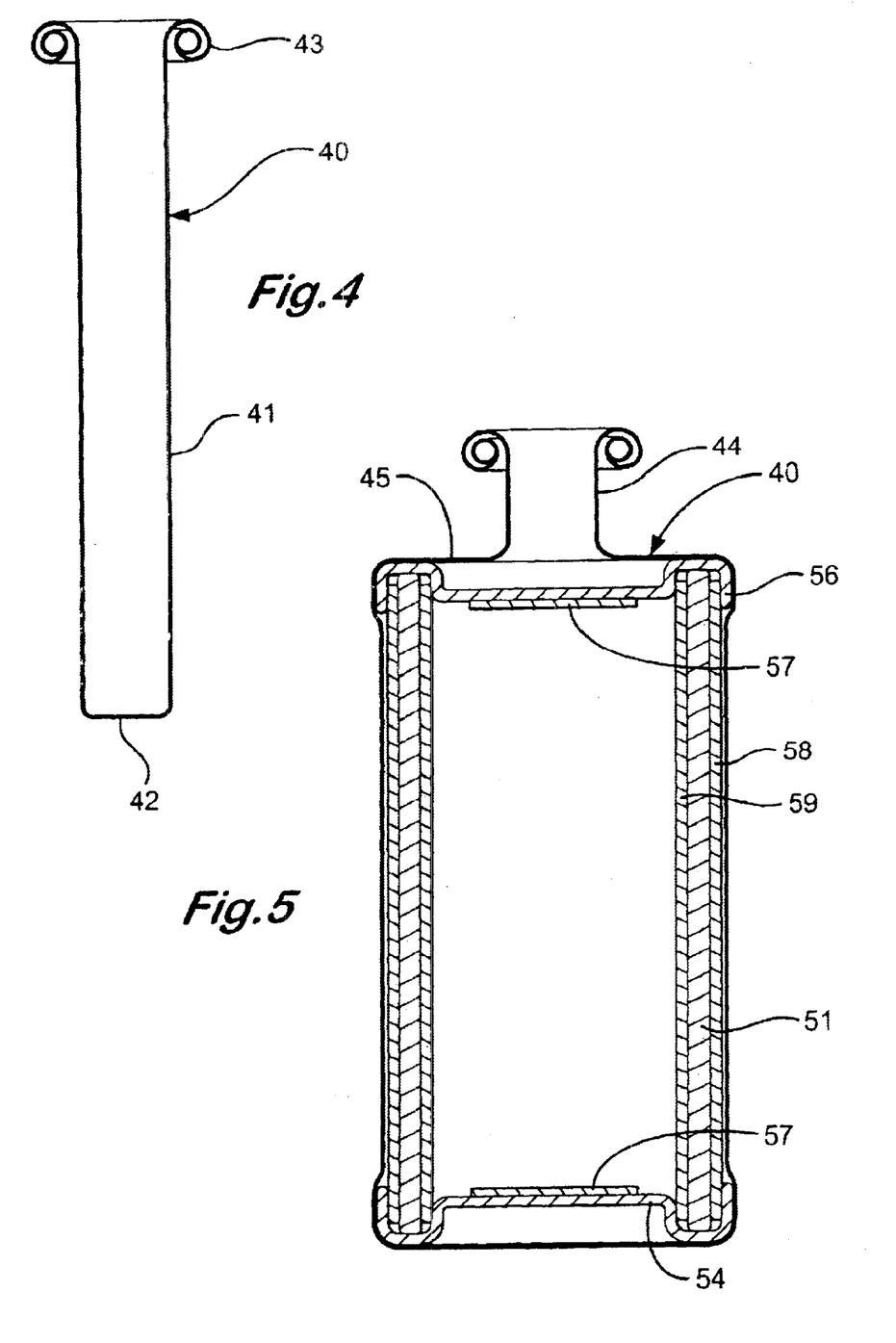
FIG. 4 is a cross-sectional view of a rubber sheath.
FIG. 5 is a cross-sectional view of the tube of FIG. 1 in the rubber sheath of FIG. 4.

Referring now to FIGS. 4 and 5, for further security, for example for use with potentially seriously hazardous samples, a sheath 40 of rubber, or like material, is provided. The sheath 40 is provided as a tube 41, of smaller diameter than the tube 51, closed at one end 42, and with a rolled lip 43 at the distal end. Being of rubber or like material the sheath is stretchable for introduction of the tube 51 therein, and thus grips tightly to the tube 51. The sheath is also longer than the tube 51 such that a section of sheath 44 remains unfilled by the tube 1. This remains in its unstretched state, and a small section of the sheath 45, is stretched across the over the end cap 56 of the tube. This unfilled section of sheath 44 as shown is left open, but may be closed with a closure member, or may be knotted. In use, if the tube is crushed to such an extent that the end caps 54, 56 are displaced from the ends of the tube due to the expulsion of air from the tube, the sheath will stretch but will remain in contact with both the end caps and the tube. After the initial force and displacement of air, the sheath will urge the end caps 54, 56 back to their previous position. The end caps 54, 56 are made from translucent plastics material and are provided with a disc 57 of an indicator material such that if leakage occurs within the tube, the indicator changes colour. The tube is lined on the inside and outside with absorbent material 58, 59 to minimise the risk to handlers if leakage does occur in the tube. In addition, the sheath 40, being made of rubber of like material, which is waterproof, is an additional barrier to minimise the risk of leakage, particularly if the unfilled section 44 is closed or knotted. In use the tube 51, in its sheath 40 may be placed into an envelope 11 for additional protection and storage with accompanying documentation.

Figure 6:
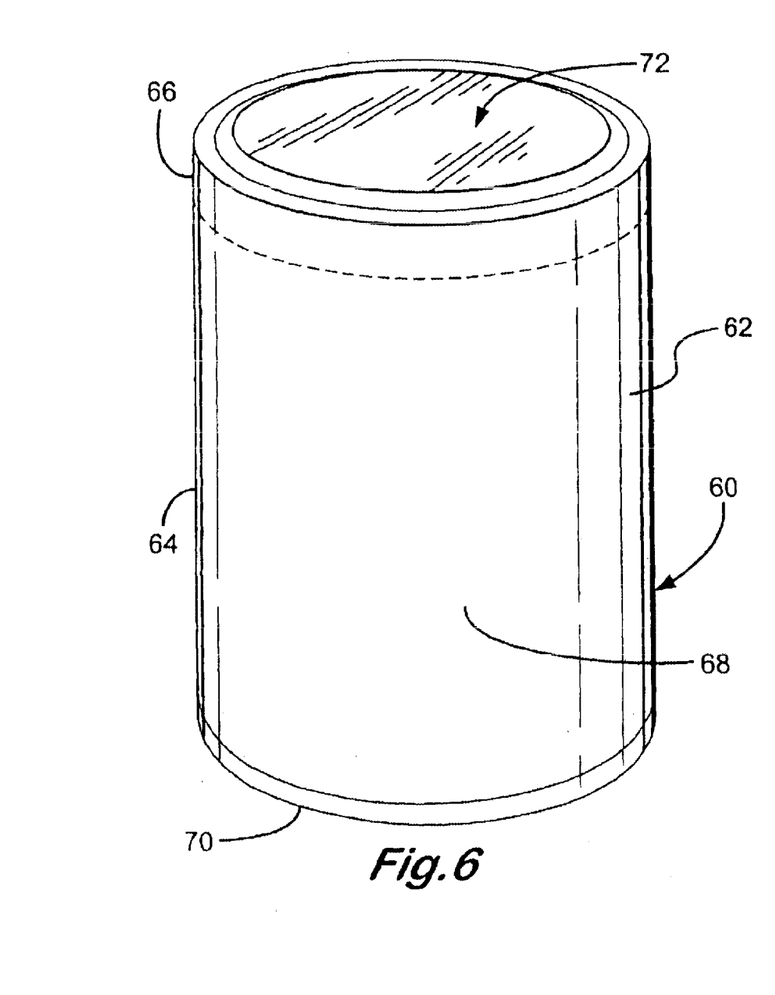
FIG. 6 is a perspective view of a container of the invention, ready for use.
Figure 7:
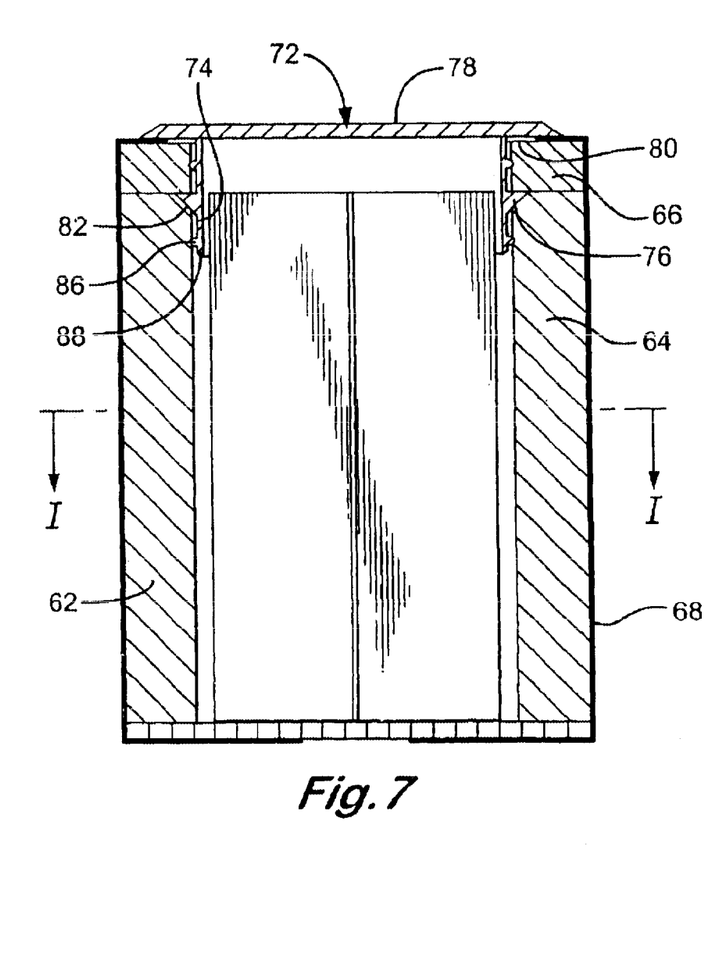
FIG. 7 is a cross-section of the container of FIG. 6.
Figure 8:
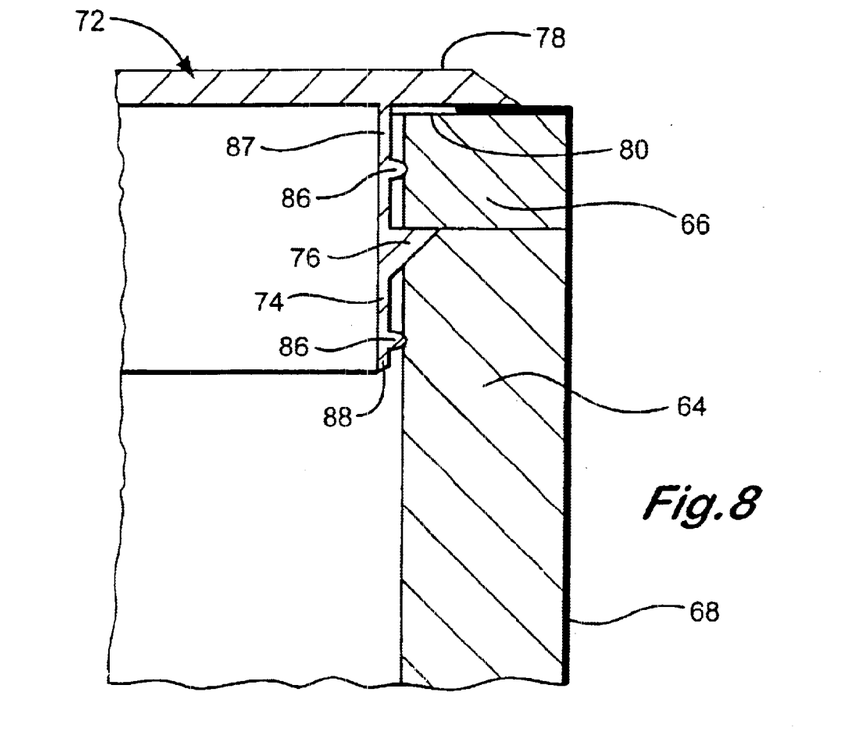
FIG. 8 is a scrap view of part of the lid in FIG. 7.

Referring to FIGS. 6, 7 and 8, the container 60 thereshown is a tamper-evident container in particular for use as a tertiary container in the transportation of hazardous materials, although it is also suitable for transportation of many goods. It is particularly suitable for the transportation of samples packed in the crush resistant tubes of the first aspect of the invention, further contained in envelopes 11 and/or rubber sheathes 40.

The body of the container 60 comprises a wrapped card-board tube 62. The tube is divided into two sections: a main section 64, and a closure section 66. The two sections, 64, 66 are held in alignment by a shrink wrap plastics material sleeve 68. The distal end 70 of the main section of the tube 74, is closed by a disc of corrugated plastics material board, such as sold under the CORREX trade mark. The disc 70 has the same diameter as the external diameter of the tube 62 and is also held in alignment by the shrink wrap sleeve 68. The main section 64 includes an absorbent lining 65.

The shrink wrap sleeve 68 is sized such that there is substantial coverage of the closure disc at the distal end 70 of the main section of the tube 64. This prevents unnoticed tampering of this portion of the container. At the top of the tube the shrink wrap sleeve 68 covers at least a portion of the thickness of the tube but does not extend further. This is to allow fitting of a lid 72.

A lid 72 is provided to close the container 60 for transportation. The lid is provided with a flange or inner rim 74 for contact with internal walls of the tube 62. The inner rim is of a size to extend over the closure section 66 and into the main section 64 of the tube. The inner rim 74 is further provided with a lip 76 distanced from the top 78 of the lid such that when the lid top 78 is flush with the distal end 80 of the closure section 66 of the tube, the lip extends into the space between the closure section 66 of the tube and the main section 64. The internal rim 82 of the main section 64 of the tube 62 is shaped to allow access to the lip 76 of the lid 72.

The lip 76 is shaped to allow ease of fitting into the rim, but to impede removal thereof. Further smaller lips 86 are provided on the upper 87 and lower section 88 of the lid 72. These help the lid 72 to grip the upper section 66 and main section 64 of the tube 62.

To prevent removal of the lid 72, the top of the lid 78 is tapered at its edge to the end of the tube 80. This provides no substantial upstand from the tube for gripping of the lid 72.

Once the lid 72 has been placed onto the tube 62, it is difficult for the lid 72 to be removed without damage to at least the lid 72, or the tube 62, the closure 70 or the shrink wrap sleeve 68. Thus any tampering with the container 60 will be clearly visible to the recipient. On arrival at its destination, a recipient can open the container by cutting along the line between the main section 64 and closure section 66 of the tube 62. For ease of use this will typically be marked on the sleeve 68. After the container has been opened the closure section 66 of the tube 62 remains attached to the lid 72. However the lid 72 can still be closed due to the lower section of the lid 88 extending into the main section 64 of the tube 62 and griping by the lips 86. However this is not a very secure closure of the lid, but is satisfactory for when not being transported. After use the container can be safely incinerated.

Figure 9:
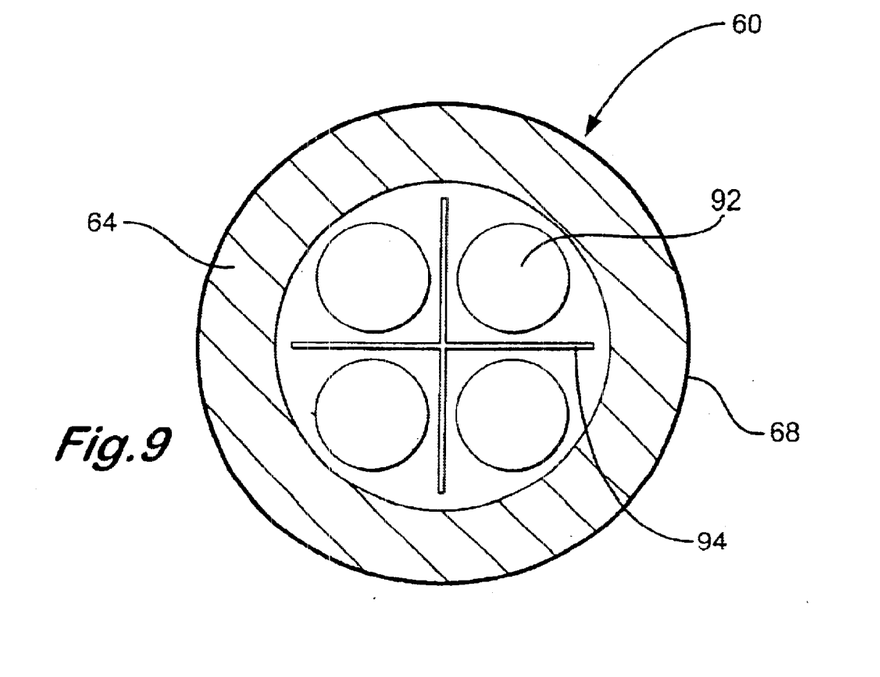
FIG. 9 is a cross-section through FIG. 7 on the line I—I.

Referring to FIG. 9 this container is particularly suitable for the transport of hazardous materials, and as a tertiary container in the transport thereof. To provide additional crush resistance when used for this purpose, the sample will typically be placed in its sample tube, in a secondary container 92, preferably the crush resistant tube 1 of the first aspect of the invention. The crush resistant tube 92 can then be placed in the container 60. To comply with IATA standard 602 the container should include a further element of crush resistance in the form of a CORREX™ support. This can be either a divider 94, if the container is used to transport more than one sample, or in the form of a square tube if transporting a single sample. With these dividers the container complies with IATA standard 602.

Figure 10:
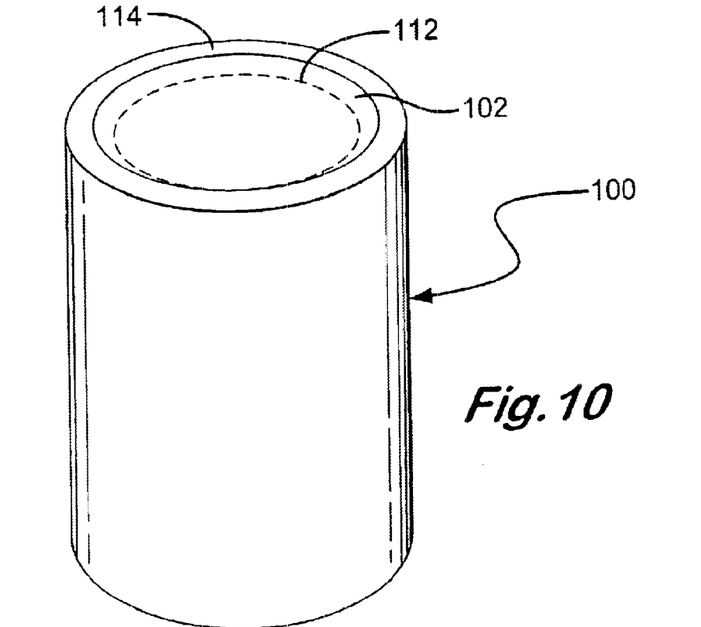
FIG. 10 is a perspective view of a crush resistant tube of the invention configured as a sharps container.

Turning now to FIG. 10, the crush resistant tube of the present invention can be configured as a container for the transport and disposal of sharps 100. The crush resistant tube 100 thereshown is of wrapped card. It is wound around an absorbent lining 102 of non-woven carrier—typically polyethylene—having air laid onto it a mixture of cellulose, super-absorbent fibre and a bicomponent fibre as a binder. The wrapped card provides a strong receptacle which will not be pierced by the sharps and is strong enough to resist crushing forces which would also allow the sharps to pierce the side of a container. The absorbent material will absorb any liquid material adhering to the sharps, thus reducing any possibility of leakage from the container. Furthermore, the super-absorbent material has a bactericidal effect, thus reducing the risk of contamination further.

Figure 11:
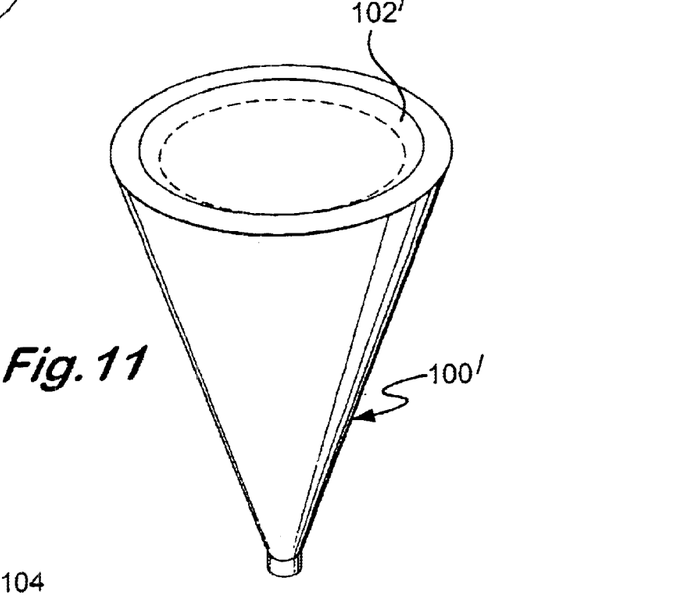
FIG. 11 is a side view of an alternative sharps container.

Referring to FIG. 11, the tube may be configured as a cone to minimise transportation space.

Figure 12:
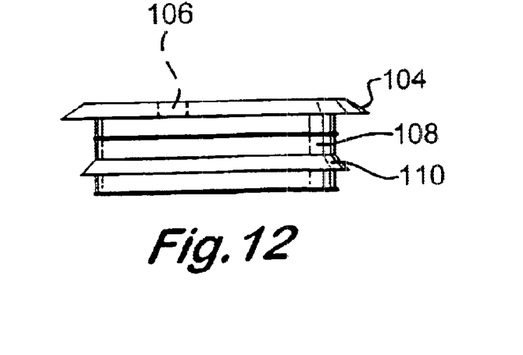
FIG. 12 is a perspective view of an end cap of the sharps container of FIG. 10 or FIG. 11.

FIG. 12 shows an end cap, having an aperture 106 for the insertion of sharps. The aperture is shaped such that the needle can be introduced into the aperture while still attached to the syringe. The needle is held while the syringe is removed, the needle then falling into the container.

The cap 104 has a flange 108 which extends into the container. The flange 108 is provided with a lip 110 for engaging in the wall of the container. The absorbent material is pliable and forms an indentation for the lip 110, which then makes the removal of the cap more difficult. In addition a groove 112 may be provided in the wall 114 of the tube into which the lip engages.

After use the whole container and the sharps contained therein can be safely transported to an incinerator for destruction.

The invention is not intended to be restricted to the details of the above described embodiment. For instance the end caps may be formed with an inner rim only or an outer rim only. The invention can also be used to transport goods other than medical samples, for example wine bottles or other bottled liquids.

What is claimed is:

1. A transport package for an item containing a quantity of liquid susceptible to leaking from the item, the package comprising:

a rigid crush resistant tube for containing the item, the tube comprising a plurality of layers wound about an axis of the tube and adhered together, said layers including an innermost wound layer forming an absorbent lining that defines an inner surface of the crush-resistant tube such that liquid leaked from the contained item will come into contact with the absorbent lining; and a pair of end closures connected to opposite ends of the crush-resistant tube to enclose the item in the tube;

wherein the absorbent lining comprises superabsorbent material to absorb and retain liquid that leaks from the contained item, whereby such absorbed liquid is prevented from escaping the transport package.

2. A transport package as claimed in claim 1, wherein a plurality of the layers of the tube comprise cardboard windings.

3. A transport package as claimed in claim 2, wherein the cardboard windings of the crush resistant tube are interspersed with a reinforcement layer.

4. A transport package as claimed in claim 2, wherein the cardboard windings are adhered together with a resin material.

5. A transport package as claimed in claim 1, wherein the crush resistant tube is of plastics material.

6. A transport package as claimed in claim 1, wherein the crush resistant tube is of epoxy impregnated glass fibre matt.

7. A transport package as claimed in claim 1, including a waterproof layer between the absorbent lining and the crush resistant tube.

8. A transport package as claimed in claim 1, wherein the crush resistant tube further includes an outer waterproof layer.

9. A transport package as claimed in claim 1, wherein the crush resistant tube further includes an outer absorbent layer.

10. A transport package as claimed in claim 1, wherein the end closures carry on their inside a leakage indicator.

11. A transport package as claimed in claim 1, further including a protective envelope including a pouch for the crush resistant tube and a pouch for documentation.

12. A transport package as claimed in claim 11, wherein the pouch is sized to receive the tube as a tight fit.

13. A transport package as claimed in claim 11, wherein the envelope is lined with absorbent material.

14. A transport package as claimed in claim 1, further including a sheath of rubber material.

15. A container comprising:
a tube forming the main body of the container, the tube being divided into two sections,
a band around the circumference of the tube at an abutment between the two sections of the tube, to hold them in alignment,
a lid for closing the tube at one end, the lid including an inner rim for engagement within the tube, the rim having a lip for engagement between the two sections of the tube; and
a closure for the other end of the tube.

16. A container as claimed in claim 15, wherein the band is a sleeve extending along the full length of the tube.

17. A container as claimed in claim 16, wherein the sleeve is of shrink wrap plastics material.

18. A container as claimed in claim 15, wherein a rim of an outside surface of the lid has no substantial upstand from the one section of the tube whereby it cannot readily be gripped.

19. A container as claimed in claim 15, wherein the tube is of wound cardboard material.

20. A container as claimed in claim 15, wherein an upper inner rim of the tube is indented to allow ingress of the lip of the lid.

21. A container comprising:
a tube forming the main body of the container, the tube being divided into two sections,
a band around the circumferences of the tube at an abutment between the two sections of the tube, to hold them in alignment,
a lid for closing the tube at one end, the lid including an inner rim for engagement within the tube, the rim having a lip for engagement between the two sections of the tube, and
a closure for the other end of the tube: and
wherein the container houses a transport package comprising:
a rigid crush resistant tube sized to receive the goods,
an absorbent lining formed integrally with the crush resistant tube, and
a pair of end caps for the crush resistant tube.

22. A method for transporting medical wastes, comprising the steps of: containing the waste in a transport package comprising a rigid crush resistant tube sized to receive the goods, an absorbent lining formed integrally with the crush resistant tube, a pair of end caps for the crush resistant tube;
placing the transport package in a container comprising:
a tube forming the main body of the container, the tube being divided into two sections, a band around the circumferences of the tube at an abutment between the two sections of the tube, to hold them in alignment, a lid for closing the tube at one end, the lid including an inner rim for engagement within the tube, the rim having a lip for engagement between the two sections of the tube; and a closure for the other end of the tube,
transporting the container to a destination; and
removing the transport package from its container at the destination.

23. A transport package for an item containing a quantity of liquid susceptible to leaking from the item, the package comprising:
a rigid crush-resistant tube for containing the item, the tube comprising a plurality of layers wound about an axis of the tube and adhered together, said layers including an innermost wound layer forming an absorbent lining that defines an inner surface of the crush-resistant tube such that liquid leaked from the contained item will come into contact with the absorbent lining; and
a pair of end closures connected to opposite ends of the crush-resistant tube to enclose the item in the tube;
wherein the absorbent lining comprises a non-woven support web onto which fibrous material is air-laid, said fibrous material incorporating superabsorbent material to absorb and retain liquid that leaks from the contained item, whereby such absorbed liquid is prevented from escaping the transport package.

24. The transport package of claim 23, wherein the fibrous material of the absorbent lining comprises superabsorbent fibers.

25. The transport package of claim 23, wherein the fibrous material of the absorbent lining includes thermoplastic fibers as a bonding material.

26. The transport package of claim 23, wherein the fibrous material of the absorbent lining includes cellulose fibers.

27. The transport package of claim 23, wherein the fibrous material of the absorbent lining comprises a blend of superabsorbent fibers, thermoplastic fibers as a bonding material, and cellulose fibers.

* * * * *